United States Patent
Buni

[11] Patent Number: 6,004,352
[45] Date of Patent: Dec. 21, 1999

[54] TIBIA PLATFORM FOR AN ARTIFICIAL KNEE JOINT

[75] Inventor: Richard Buni, Hettlingen, Switzerland

[73] Assignee: Sulzer Orthopaedie AG, Winterthur, Switzerland

[21] Appl. No.: 09/004,747

[22] Filed: Jan. 8, 1998

[30] Foreign Application Priority Data

Jan. 10, 1997 [EP] European Pat. Off. .............. 97810009

[51] Int. Cl.⁶ ...................................................... A61F 2/38
[52] U.S. Cl. ............................................................. 623/20
[58] Field of Search ................................................ 623/20

[56] References Cited

U.S. PATENT DOCUMENTS

| | | | |
|---|---|---|---|
| 4,714,474 | 12/1987 | Brooks | 623/20 |
| 4,795,468 | 1/1989 | Hodorek | 623/20 |
| 4,822,362 | 4/1989 | Walker | 623/20 |
| 4,944,757 | 7/1990 | Martinez | 623/20 |
| 5,007,933 | 4/1991 | Sidebotham | 623/20 |
| 5,108,442 | 4/1992 | Smith | 623/20 |
| 5,152,797 | 10/1992 | Lucman . | |
| 5,330,534 | 7/1994 | Herrington . | |
| 5,413,608 | 5/1995 | Keller | 623/20 |
| 5,645,604 | 7/1997 | Schneider | 623/20 |

FOREIGN PATENT DOCUMENTS

| | | |
|---|---|---|
| 0 381 352 A1 | 8/1990 | European Pat. Off. . |
| 0 738 504 A1 | 10/1996 | European Pat. Off. . |
| 2 720 267 | 12/1995 | France . |
| 3730175 C1 | 9/1988 | Germany . |

*Primary Examiner*—Michael J. Milano
*Attorney, Agent, or Firm*—Townsend and Townsend and Crew LLP

[57] ABSTRACT

The invention is shown by a tibia platform comprising a metallic lower part and different bearing parts made of plastic which can be anchored to one another at a posterior position via an open hinge joint. The bearing part has a guide rib for guiding femur condyles which projects upwards by a height of at least 15 mm above the lowest point of the sliding surfaces. Large lateral forces such as occur in high guide ribs and in varus and valgus positions of the knee can be taken up because of a separate metallic pawls which engages at a horizontal projection of the lower part at a distance "1" away from the hinge joint. The pawl is displaceably journalled with respect to the bearing part and is permanently positionable by means of auxiliary means by an enforced movement into a latched position at the projection.

7 Claims, 3 Drawing Sheets

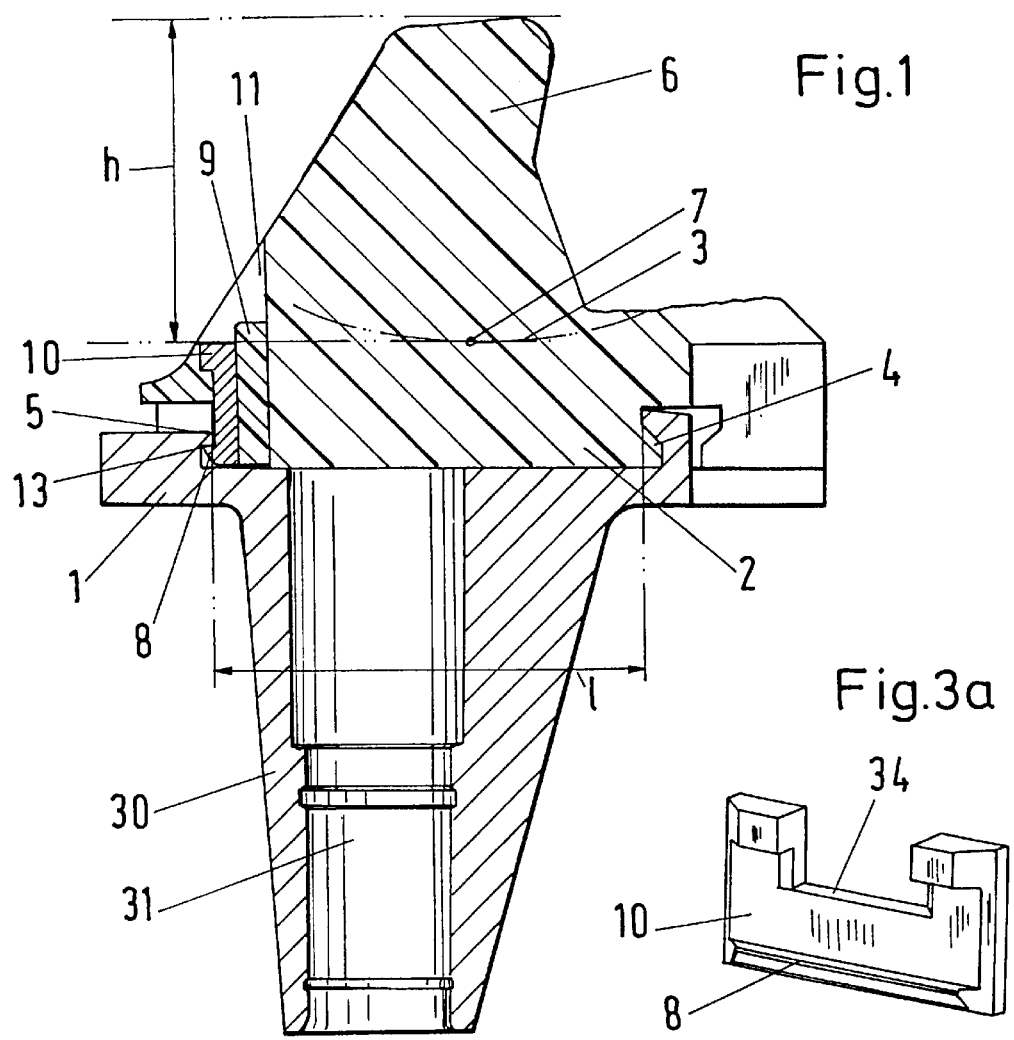
Fig.1
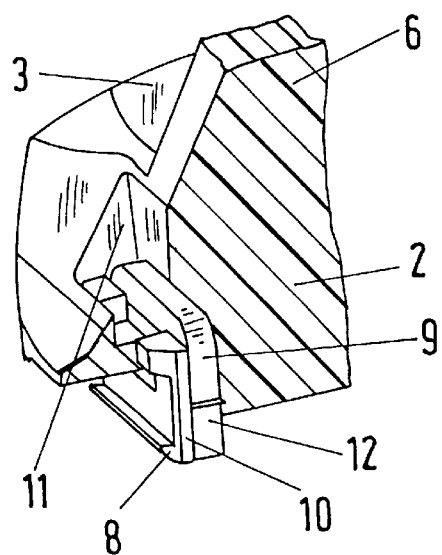
Fig.2
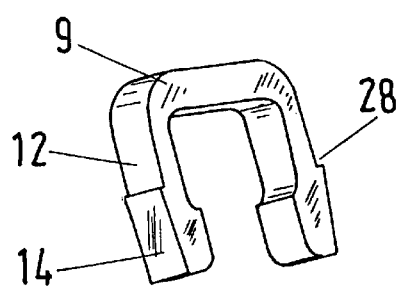
Fig.3a
Fig.3b

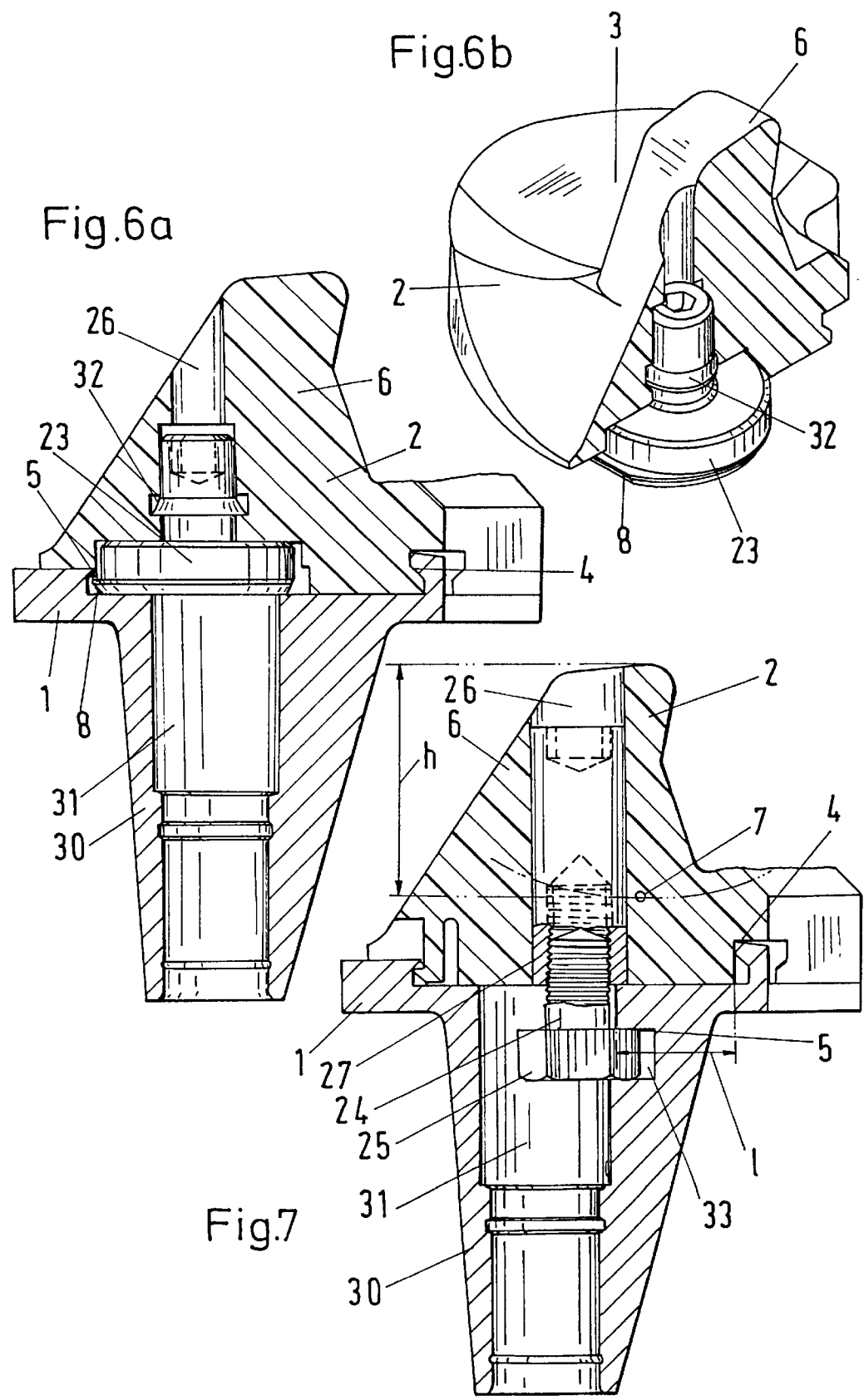

6,004,352

TIBIA PLATFORM FOR AN ARTIFICIAL KNEE JOINT

BACKGROUND OF THE INVENTION

The invention relates to a tibia platform for an artificial knee joint comprising a metallic lower part which can be anchored in the tibia and a bearing part which is made of plastic, which has sliding surfaces for two femur condyles, which can be pivoted at the posterior at the lower part via an open hinge joint and which can be anchored at a distance "1" away from the hinge joint in the anterior direction at a projection of the lower part by a pawl.

A tibia platform of this kind is shown in the patent specification EP-A-0 738 504. In this design a pawl formed in a single piece on the bearing part latches under the projection of the lower part during assembly. Such bearing parts are often executed in plastic, for example in polyethylene, in order to achieve an advantageous sliding pairing with metallic femur condyles. The plastics used have the advantage that their structure and strength avoid high point loads. This means that limits are placed on these plastics when latching takes place using a pawl.

The direction and the maximum values of the forces that act on the bearing part and further on the lower part of the tibia platform depend strongly on how intact the ligamentary apparatus still is. The fewer ligaments that are still operative the more the femur condyles must be guided by a middle guide rib in the form of an artificial eminentia and the more extreme are the loads which act on the bearing part.

SUMMARY OF THE INVENTION

The object of the invention is to provide an effective guidance of the femur condyles and a lasting anchoring of the bearing part in the lower part. This object is satisfied in that between the sliding surfaces a guide rib projects upwards with a height of at least h=15 mm above a lowest point of the sliding surfaces, in that a separate metallic pawl is displaceably mounted relative to the bearing part, and in that the pawl can be permanently positioned in a latched position at the projection by an enforced movement by auxiliary means.

The arrangement has the advantage that varus and valgus positions of the knee joint can also be taken up in the case of a weak ligament apparatus. A further advantage consists in the fact that, with a lower part that has already been inserted in the tibia, a space saving insertion of the bearing part is possible from the anterior direction in spite of the protruding eminentia. The bearing part can be inserted into the open hinge joint from the anterior direction at a very shallow angle, while the auxiliary means for anchoring the metallic pawl to the bearing part can be applied from above and from the anterior direction. A further advantage consists in the fact that, for an already implanted lower part, bearing parts with and without a pronounced guide rib and with different distances of the bearing surface from the lower part can be inserted in the sense of a modular system. A surgeon can therefore decide on a suitable bearing part in accordance with the state of the ligament apparatus after the insertion of the lower part.

BRIEF DESCRIPTION OF THE DRAWINGS

FIG. 1 is a schematic section of a tibia platform in the sagittal direction through a lower part and a bearing part which are connected via a metallic staple and a spacer executed as a spring;

FIG. 2 is a section of the bearing part of FIG. 1 with the staple and the spacer;

FIG. 3a is an enlarged view of the staple of FIG. 1;

FIG. 3b is an enlarged view of the spacer of FIG. 1;

FIG. 4b is a schematic view of the block with the screw in FIG. 4a;

FIG. 5b is a schematic view of the block in FIG. 5a;

FIG. 6a is a schematic section of another tibia platform in the sagittal direction through a lower part and a bearing part which are connected by a metallic pawl at the periphery of a rotatable pin anchored in the periphery;

FIG. 6b is a schematic view of the bearing part and rotatable pin in FIG. 6a;

FIG. 7 is a schematic section of another tibia platform in the sagittal direction through a lower part and a bearing part which are connected together by a metallic latching in the form of a laterally insertable screw and a clamping sleeve.

DESCRIPTION OF THE PREFERRED EMBODIMENTS

Figure 4A:
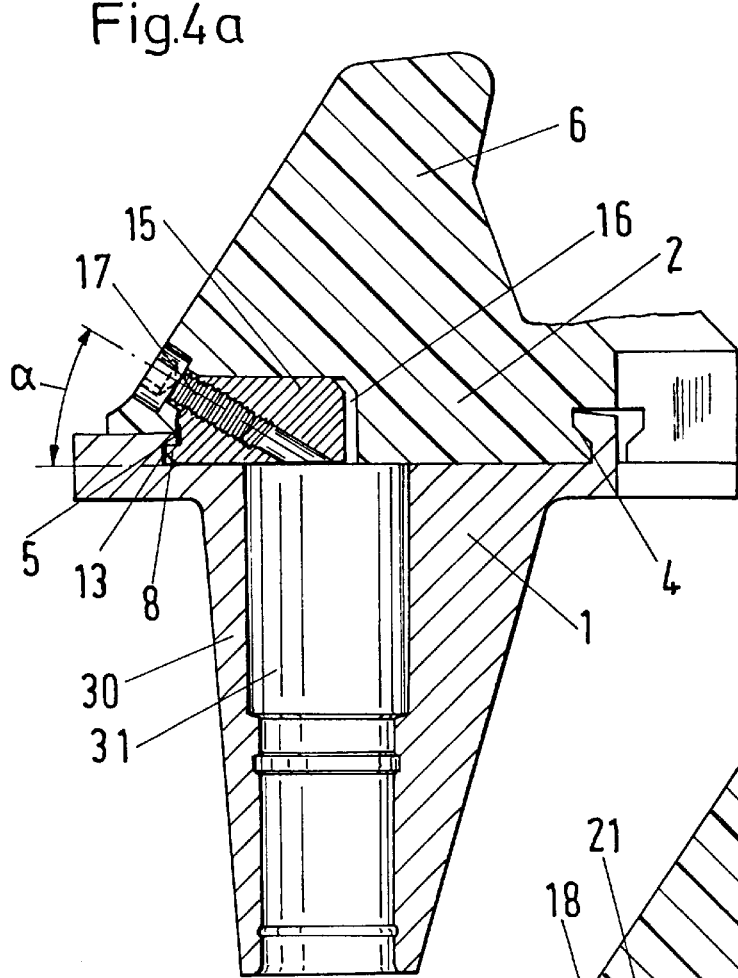
FIG. 4a is a schematic section of another tibia platform in the sagittal direction through a lower part and a bearing part which are clamped with respect to one another via a metallic pawl in the form of a block and via a screw.

The Figures show a tibia platform with a metallic lower part 1 and with different bearing parts 2 of plastic which can be anchored to one another at the posterior via an open hinge joint 4. The bearing part 2 has a guide rib 6 for the guidance of femur condyles which projects upwardly at least 15 mm above the lowest point 7 of the sliding surfaces 3. Large lateral forces such as occur with high guide ribs 6 and varus and valgus positions of the knee can be taken up because of a separate metallic pawl 8 which engages at a horizontal projection 5 of the lower part 1 at a distance "1" away from the hinge joint 4. The pawl 8 is displaceably journalled with respect to the bearing part 2 and is permanently positionable by auxiliary means 9 through an enforced movement in a latched position 13 at the projection 5.

In FIGS. 1 to 3b a metallic lower part 1 of a tibia platform is anchorable at its lower side via a spigot 30 in a non-illustrated tibia. The spigot 30 is reinforced cross-wise by ribs and has a receiving bore 31 in which stems of differing lengths can be secured to assist the anchoring. The support surface of the bearing part 2 is sunk in the lower part 1 and is held in this position at the posterior by an open hinge 4 and at the anterior by a projection 5 and a separate metallic pawl 8. The pawl 8 is executed as a staple 10 and is held in its latched position 13 by the spacer 12. After the insertion of the bearing part 2 into the lower part 1, the metallic pawl is first inserted through a cut-out 11 in the bearing part and brought approximately to the latched position 13. Then the C-shaped spacer 12 is thrust downwards in the remaining intermediate space in order to press on the pawl and in order for its lateral shoulders 28 to latch into the bearing part. Because the back of the spacer acts as a spring 14, its own weight holds it in its latched position under all usual stresses. Nevertheless a simple removal results, since the staple 10 lying in front of it has a cut-out 34 in order to be able to insert a screwdriver-like tool and to release the spacer. Between the sliding surfaces 3 of the bearing part 2 there is a guide rib 6 projecting upwardly by a height h of more than 15 mm above the lowest point 7 of the sliding surfaces 3. In accordance with the large height h, the guide rib 6 is increasingly loaded in the medial plane as a beam bending, the bending moment of which must be transmitted via the connection to the lower part, in which the metallic pawl also participates. FIGS. 1, 4a, 5a, 6a show an identical lower part in which the projection 5 is spaced from the open hinge joint 4 by a large distance "1", with the same projection 5 being utilizable in the sense of a kit for the latching of one-piece polyethylene bearing parts and of separate metallic pawls.

Figure 4B:
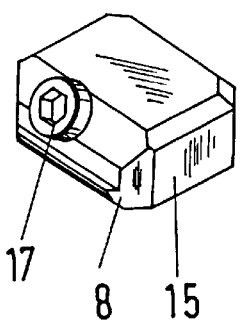

In FIG. 4a a metallic block 15 is inserted into the bearing part 2 for displacement in the sagittal direction. A screw 17, having a head which lies against the outer side of the bearing part, draws the block 15 towards its upper limitation in the bearing part at an angle of 0<α<90° and simultaneously draws the pawl 8 into the latched position 13 under the projection 5. For the latching process the screw 17 is turned out of the block 15 to an extent such that the block 15 is displaced in the posterior direction in the bearing part and the pivoting of the bearing part about the open hinge 4 is enabled. On tightening the screw 17 the block slides in the anterior direction and into the latched position 13. The block 15 with the pawl 8 and the inserted screw 17 can be recognized in FIG. 4b.

Figure 5A:
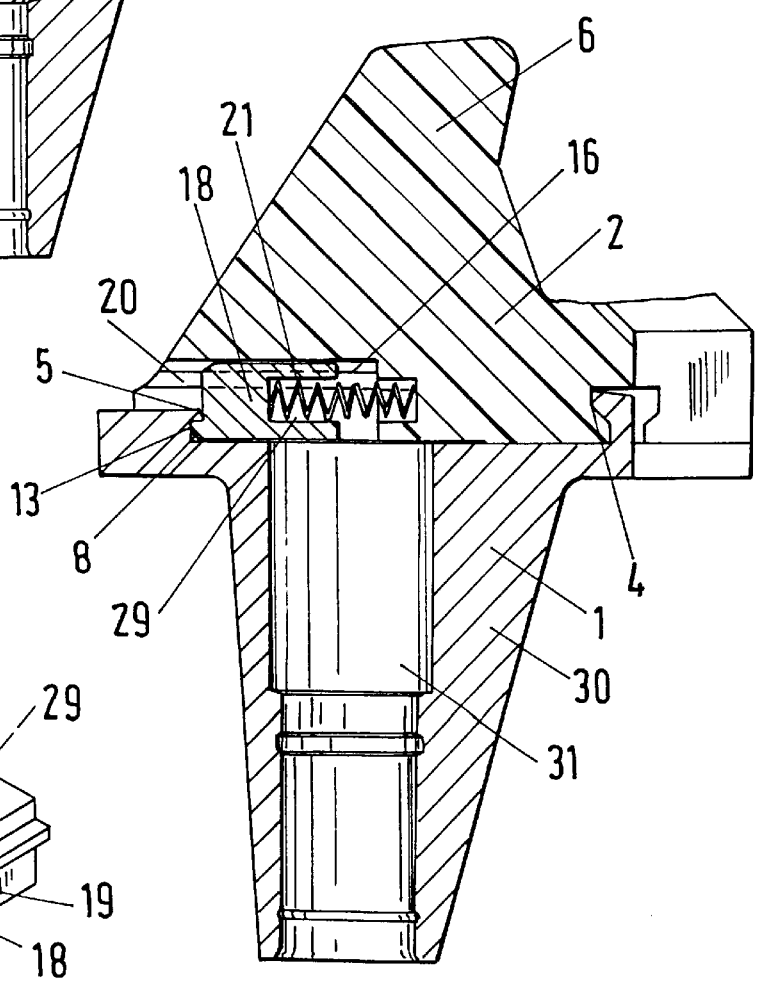
FIG. 5a is a schematic section of another tibia platform in the sagittal direction through a lower part and a bearing part which are connected together by a metallic pawl in the form of a block with protruding shoulders and by means of a coil spring.
Figure 5B:
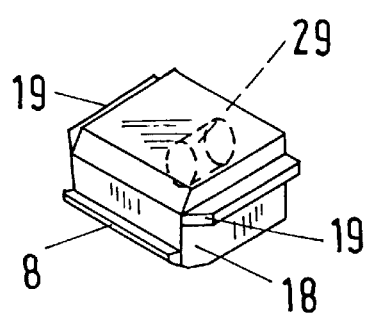

In FIGS. 5a, b, a metallic block 18 with lateral shoulders 19 is guided in the bearing part 2 in grooves 20 in such a manner that it can only move in the sagittal direction. The block 18 can be pushed from the anterior position into the bearing part and is pressed back into the anterior position by a coil spring which acts in the sagittal direction and is retained by a bore 29. When the bearing part 2 pivots about the open hinge 4, the block must be held back until the bearing part touches the base in order then to have the pawl 8 brought into the latched position 13 by the spring 21. The volume of the block 15 can largely be used to receive the spring 21 in a deep bore 29. For removal, the pawl can be thrust backwards by a rod without the spring being overextended.

In FIGS. 6a, b, a rotatable pin 23 is anchored in the bearing part 2 in the vertical direction and is expanded to a disc at the lower end and is secured from above against falling out by a lip 32. The rotatable pin ends in the form of an inner hexagon which can be reached by a tool from above through a bore 26. The pawl 8 is formed as an eccentric shoulder at the periphery of the rotatable pin and can be rotated with the tool beneath the projection 5 for the latching of the assembly. Self-locking of the pawl 8 is achieved, for example, in that it rises slightly around the periphery in order to wedge itself under the projection 5.

In FIG. 7 a lower part 1 is additionally provided with a pocket 33 in the upper region of the receiving bore 31. The pocket 33 ends at the top as a shoulder 5 at a distance "1" from the open hinge joint. As a pawl the head 25 of a metal bolt 24 is pushed laterally into the pocket 33 and the bearing part 2 is then pivoted about the open hinge 4 until the screw 24 is captured within a passage bore 26 of the bearing part. Then a long sleeve executed as a nut is pushed on through the passage bore, and the screw is centered and is clamped at the lower part 1 by the sleeve, which can be rotated by an insertion tool. The central position of the sleeve supports the guide rib 6 and is thus anchored to the bearing part to such an extent that it prevents any horizontal movement and any pivoting about the open hinge joint 4.

What is claimed is:

1. A tibia platform for an artificial knee joint comprising:
   a metallic lower part configured to be anchored in the tibia;
   a bearing part which is made of plastic, the bearing part having sliding surfaces for two femur condyles and being pivotable at a posterior at the metallic lower part via an open hinge joint of the metallic lower part, the bearing part including a guide rib between the sliding surfaces, the guide rib projecting upward with a height of at least 15 mm above a lowest point of the sliding surfaces; and
   a separate metallic pawl which is displaceably mounted relative to the bearing part for anchoring the bearing part at a projection of the metallic lower part which is located at a distance away from the open hinge joint of the metallic lower part in an anterior direction, the separate metallic pawl being positionable in a latched position at the projection of the metallic lower part to withstand loads resulting from sidewards bending forces on the guide rib of the bearing part, wherein the pawl has the form of a staple which is insertable into the bearing part from above through a cut-out of the bearing part.

2. A tibia platform in accordance with claim 9 further comprising a spacer for positioning the separate metallic pawl in a latched position at the projection of the metallic lower part.

3. A tibia platform in accordance with claim 2 wherein the spacer comprises a spring which is latched in the bearing part.

4. A tibia platform for an artificial knee joint comprising:
   a metallic lower part configured to be anchored in the tibia;
   a bearing part which is made of plastic, the bearing part having sliding surfaces for two femur condyles and being pivotable at a posterior at the metallic lower part via an open hinge joint of the metallic lower part, the bearing part including a guide rib between the sliding surfaces, the guide rib projecting upward with a height of at least 15 mm above a lowest point of the sliding surfaces; and
   a separate metallic pawl which is displaceably mounted relative to the bearing part for anchoring the bearing part at a projection of the metallic lower part which is located at a distance away from the open hinge joint of the metallic lower part in an anterior direction, the separate metallic pawl being positionable in a latched position at the projection of the metallic lower part to withstand loads resulting from sidewards bending forces on the guide rib of the bearing part, wherein the pawl comprises a block which has laterally projecting shoulders and is displaceably guided in a posterior direction in the bearing part by grooves in the bearing part.

5. A tibia platform in accordance with claim 4 further comprising a spring disposed between the block and the bearing part, the spring pressing the block in an anterior direction into the latched position.

6. A tibia platform for an artificial knee joint comprising:
   a metallic lower part configured to be anchored in the tibia;
   a bearing part which is made of plastic, the bearing part having sliding surfaces for two femur condyles and being pivotable at a posterior at the metallic lower part via an open hinge joint of the metallic lower part, the bearing part including a guide rib between the sliding surfaces, the guide rib projecting upward with a height of at least 15 mm above a lowest point of the sliding surfaces; and a separate metallic pawl which is displaceably mounted relative to the bearing part for anchoring the bearing part at a projection of the metallic lower part which is located at a distance away from the open hinge joint of the metallic lower part in an anterior direction, the separate metallic pawl being positionable in a latched position at the projection of the metallic lower part to withstand loads resulting from sidewards bending forces on the guide rib of the bearing part, wherein the pawl is executed as a shoulder at a periphery of a rotatable pin which is anchored in the bearing part, the pawl being engageable under the projection of the metallic lower part by rotation of the rotatable pin which is secured in an axial direction.

7. A tibia platform for an artificial knee joint comprising:

a metallic lower part configured to be anchored in the tibia;

a bearing part which is made of plastic, the bearing part having sliding surfaces for two femur condyles and being pivotable at a posterior at the metallic lower part via an open hinge joint of the metallic lower part, the bearing part including a guide rib between the sliding surfaces, the guide rib projecting upward with a height of at least 15 mm above a lowest point of the sliding surfaces; and a bolt having a head forming a separate metallic pawl which is displaceably mounted relative to the bearing part for anchoring the bearing part at a projection of the metallic lower part which is located at a distance away from the open hinge joint of the metallic lower part in an anterior direction, the separate metallic pawl being positionable in a latched position at the projection of the metallic lower part, the head of the bolt being movable under the projection of the metallic lower part, the bolt extending through a passage in the bearing part which enables pivoting of the bearing part into place when the bolt is inserted, the passage being dimensioned in such a manner that a sleeve which is formed as a counter-nut is insertable therein to clamp the bolt at the projection of the metallic lower part and at the same time prevent slipping of the bearing part at the metallic lower part.

* * * * *